United States Patent
Gliner et al.

(10) Patent No.: US 11,031,172 B2
(45) Date of Patent: Jun. 8, 2021

(54) TRACKING SENSOR

(71) Applicant: BIOSENSE WEBSTER (ISRAEL) LTD., Yokneam (IL)

(72) Inventors: Vadim Gliner, Haifa (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 326 days.

(21) Appl. No.: 14/743,256

(22) Filed: Jun. 18, 2015

(65) Prior Publication Data
US 2016/0372252 A1 Dec. 22, 2016

(51) Int. Cl.
*H01F 27/255* (2006.01)
*A61B 34/20* (2016.01)
(Continued)

(52) U.S. Cl.
CPC .......... *H01F 27/255* (2013.01); *A61B 5/065* (2013.01); *A61B 34/20* (2016.02); *A61B 90/39* (2016.02); *A61M 25/09* (2013.01); *H01F 1/37* (2013.01); *H01F 3/08* (2013.01); *H01F 5/00* (2013.01); *H01F 27/2823* (2013.01); *H01F 41/0246* (2013.01); *H01F 41/066* (2016.01); *A61B 17/24* (2013.01); *A61B 2017/00526* (2013.01); *A61B 2017/00876* (2013.01); *A61B 2034/2046* (2016.02); *A61B 2034/2051* (2016.02); *A61B 2034/2072* (2016.02);
(Continued)

(58) Field of Classification Search
CPC .......... A61B 2017/00526; A61B 2017/00876; A61B 2034/2046; A61B 2034/2051; A61B 2034/2072; A61B 2090/397; A61B 34/20; A61B 5/065; A61B 90/39
See application file for complete search history.

(56) References Cited

U.S. PATENT DOCUMENTS 5,062,197 A * 11/1991 Ngo .................... H01F 3/10
29/606
5,109,843 A   5/1992 Melvin
(Continued)

FOREIGN PATENT DOCUMENTS

CN     203786959 U    8/2014
DE     1953865 A1 *  8/2008 ............... H01F 5/02
(Continued)

OTHER PUBLICATIONS

MatWeb, Flexural Strength Testing of Plastics, 2012. http://www.matweb.com/reference/flexuralstrength.aspx. (Year: 2012).*
(Continued)

*Primary Examiner* — Yi-Shan Yang
(74) *Attorney, Agent, or Firm* — Notaro, Michalos & Zaccaria P.C.

(57) ABSTRACT

A medical instrument and method to facilitate the performance of medical procedures. The instrument has at least one tracking sensor being disposed at a distal portion of the instrument. The sensor includes a tube containing a ferrite powder, and a coil wound around the tube. The method includes inserting the medical instrument into a subject. The sensor generates a signal in response to a magnetic field to enable the physician to track the instrument in the subject.

30 Claims, 2 Drawing Sheets

(51) Int. Cl.
    *H01F 5/00*     (2006.01)
    *H01F 1/37*     (2006.01)
    *H01F 3/08*     (2006.01)
    *A61B 90/00*     (2016.01)
    *A61M 25/09*     (2006.01)
    *H01F 41/066*     (2016.01)
    *A61B 5/06*     (2006.01)
    *H01F 27/28*     (2006.01)
    *H01F 41/02*     (2006.01)
    *A61M 25/01*     (2006.01)
    *A61B 17/00*     (2006.01)
    *A61B 17/24*     (2006.01)

(52) U.S. Cl.
    CPC .................. *A61B 2090/397* (2016.02); *A61M 2025/0166* (2013.01); *A61M 2025/09175* (2013.01)

(56) References Cited

U.S. PATENT DOCUMENTS

| | | | |
|---|---|---|---|
| 6,358,432 B1 * | 3/2002 | Tomono | H01F 1/113 252/62.63 |
| 6,461,314 B1 * | 10/2002 | Pant | A61B 17/2202 600/439 |
| 9,620,270 B2 * | 4/2017 | Uemoto | H01F 17/04 |
| 2003/0020586 A1 * | 1/2003 | Uehara | G03G 15/2053 336/229 |
| 2006/0004286 A1 * | 1/2006 | Chang | A61B 5/06 600/435 |
| 2007/0208251 A1 * | 9/2007 | Anderson | A61M 25/01 600/424 |
| 2008/0255475 A1 * | 10/2008 | Kondrosky | A61M 25/09 600/585 |
| 2009/0216113 A1 * | 8/2009 | Meier | A61B 19/54 600/424 |
| 2009/0326368 A1 | 12/2009 | Zaslavsky | |
| 2011/0066029 A1 * | 3/2011 | Lyu | A61M 25/0133 600/424 |
| 2014/0159707 A1 * | 6/2014 | Ashe | H01F 41/02 324/207.16 |
| 2016/0007842 A1 * | 1/2016 | Govari | A61B 34/20 600/424 |
| 2016/0007879 A1 * | 1/2016 | Gonzalez | A61B 5/0537 600/306 |
| 2017/0367767 A1 * | 12/2017 | Blumenkranz | A61B 34/20 |

FOREIGN PATENT DOCUMENTS

| | | | | |
|---|---|---|---|---|
| EP | 1096513 A2 | 5/2001 | | |
| EP | 1953865 A1 | 8/2008 | | |
| EP | 19539654 | 8/2008 | | |
| EP | 2136379 A1 * | 12/2009 | ......... | C01G 49/0036 |
| JP | H1167522 | 3/1999 | | |
| JP | 200531767 | 11/2005 | | |
| JP | 2008265433 | 11/2008 | | |
| WO | 2007061890 A2 | 5/2007 | | |
| WO | 2011010471 A1 | 1/2011 | | |
| WO | 2013028937 A1 | 2/2013 | | |

OTHER PUBLICATIONS

European Search Report, Application No. 16174921.3-1664, dated Jan. 30, 2017.

Anonymous: "Pulverkern—Wikipedia", May 23, 2015, XP055312485, Wikipedia, die freie Enzyklopadie Retrieved from the Internet: URL:https://de.wikipedia.org/wiki/Pulverkern, retrieved on Oct. 20, 2016.

* cited by examiner

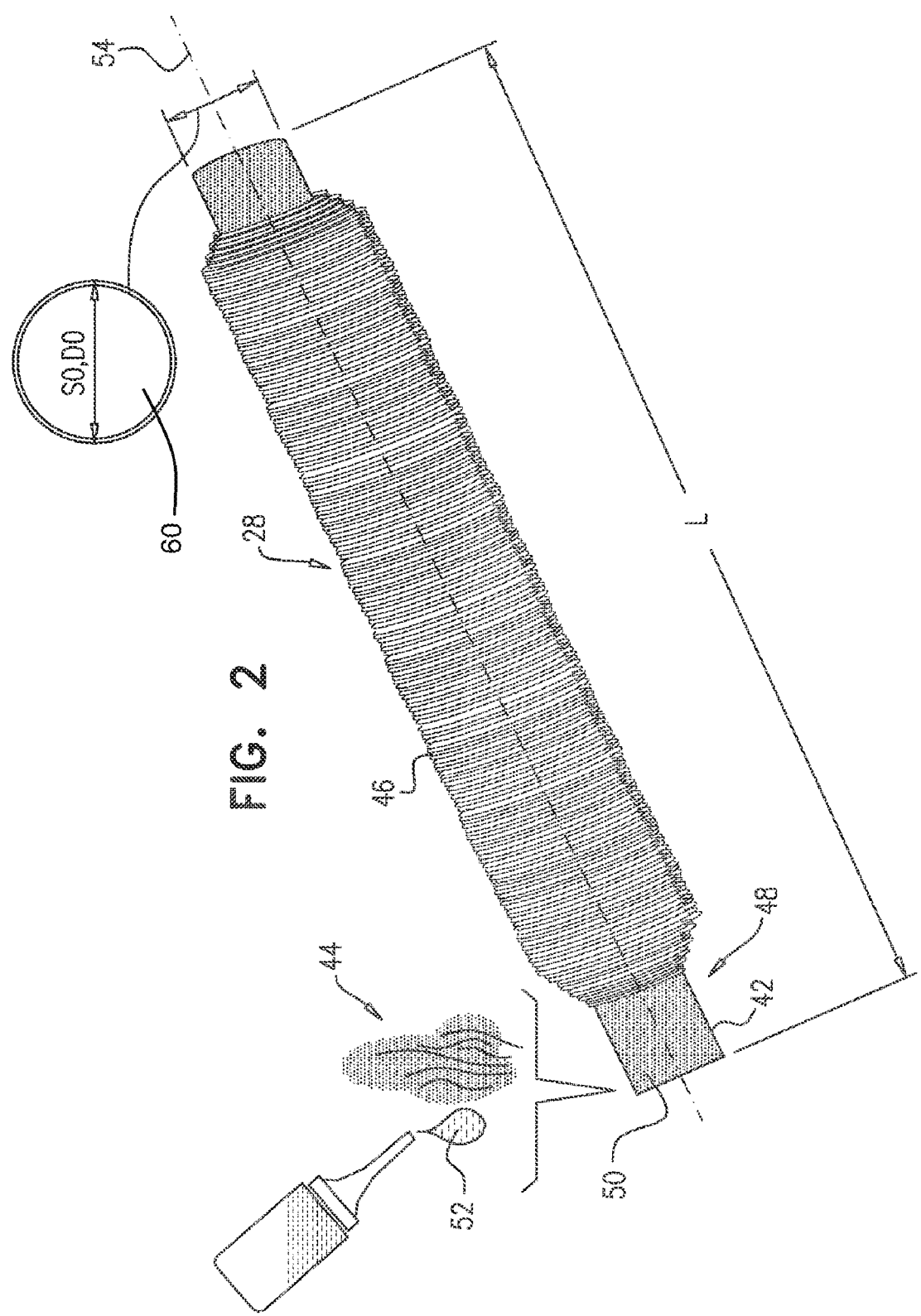

TRACKING SENSOR

FIELD OF THE INVENTION

Embodiments of the present invention relate to a tracking sensor that includes a generally rigid ferrite core, which may be used, for example, to facilitate the performance of a medical procedure.

BACKGROUND

When a medical instrument is inserted into a subject for a medical procedure such as a sinuplasty procedure, an operating physician may desire to know the approximate location and/or orientation of the instrument.

SUMMARY OF THE INVENTION

There is provided, in accordance with some embodiments of the present invention, a tracking sensor. The sensor includes a tube containing a ferrite powder, and a coil wound around the tube.

In some embodiments, the tracking sensor further includes a bonding material, the tube further containing the bonding material.

In some embodiments, the tube has a maximal transverse-cross-sectional span of less than 1 mm.

There is further provided, in accordance with some embodiments of the present invention, a medical instrument, at least one tracking sensor being disposed at a distal portion of the instrument. The sensor includes a tube containing a ferrite powder, and a coil wound around the tube.

In some embodiments, the medical instrument includes a guidewire, the tracking sensor being disposed within a lumen of the guidewire.

There is further provided, in accordance with some embodiments of the present invention, a method. The method includes inserting a medical instrument into a subject, at least one tracking sensor being disposed at a distal portion of the instrument. The sensor includes a tube containing a ferrite powder, and a coil wound around the tube. The sensor is used to generate a signal in response to a magnetic field. Using a processor, in response to the signal, the instrument is tracked.

In some embodiments, tracking the instrument includes ascertaining a position of the distal portion of the instrument.

In some embodiments, tracking the instrument includes ascertaining an orientation of the distal portion of the instrument.

In some embodiments, the instrument includes a guidewire, the method including inserting the guidewire into the subject.

In some embodiments, inserting the medical instrument into the subject includes inserting the medical instrument through a nostril of the subject.

In some embodiments, the method further includes using the instrument to perform a sinuplasty procedure on the subject.

There is further provided, in accordance with some embodiments of the present invention, a generally rigid ferrite core. The ferrite core includes a ferrite powder, and a tube, having a maximal transverse-cross-sectional span of less than 1 mm, containing the ferrite powder.

In some embodiments, the tube is substantially maximally-filled.

In some embodiments, the ferrite core further includes a bonding material, the tube further containing the bonding material.

In some embodiments, the ferrite powder and the bonding material are mixed with one another within the tube.

In some embodiments, the maximal transverse-cross-sectional span of the tube is less than 0.5 mm.

In some embodiments, the maximal transverse-cross-sectional span of the tube is less than 0.3 mm.

In some embodiments, the ferrite powder includes iron-carbonyl.

In some embodiments, a central longitudinal axis of the ferrite core is not linear.

In some embodiments, the maximal transverse-cross-sectional span of the tube is a diameter of the tube, the diameter being less than 1 mm.

In some embodiments, a ratio of the maximal transverse-cross-sectional span of the tube to a length of the tube is less than 0.2.

In some embodiments, the ratio is less than 0.1.

In some embodiments, a length of the tube is greater than 2 mm.

There is further provided, in accordance with some embodiments of the present invention, a method. The method includes inserting a ferrite powder into a tube, the tube having a maximal transverse-cross-sectional span of less than 1 mm, and compressing the ferrite powder within the tube.

In some embodiments, the method further includes inserting a bonding material into the tube.

In some embodiments, inserting the ferrite powder and the bonding material into the tube includes inserting a mixture of the ferrite powder and the bonding material into the tube.

In some embodiments, inserting the bonding material into the tube includes sealing the ferrite powder within the tube, by inserting the bonding material into the tube at at least one end of the tube.

In some embodiments, the method further includes winding a coil around the tube.

In some embodiments, the method further includes inserting the tube into a lumen of a coil.

In some embodiments, the method further includes shaping the tube such that a central longitudinal axis of the tube is not linear.

In some embodiments, the method includes repeatedly and alternatingly performing the inserting of the ferrite powder and the compressing of the ferrite powder within the tube.

In some embodiments, the method comprises, by repeatedly and alternatingly performing the inserting of the ferrite powder and the compressing of the ferrite powder within the tube, substantially maximally-filling the tube.

The present invention will be more fully understood from the following detailed description of embodiments thereof, taken together with the drawings, in which:

BRIEF DESCRIPTION OF THE DRAWINGS

FIG. 2 is a schematic illustration of a tracking sensor, in accordance with some embodiments of the present invention.

DETAILED DESCRIPTION OF EMBODIMENTS

Figure 1:
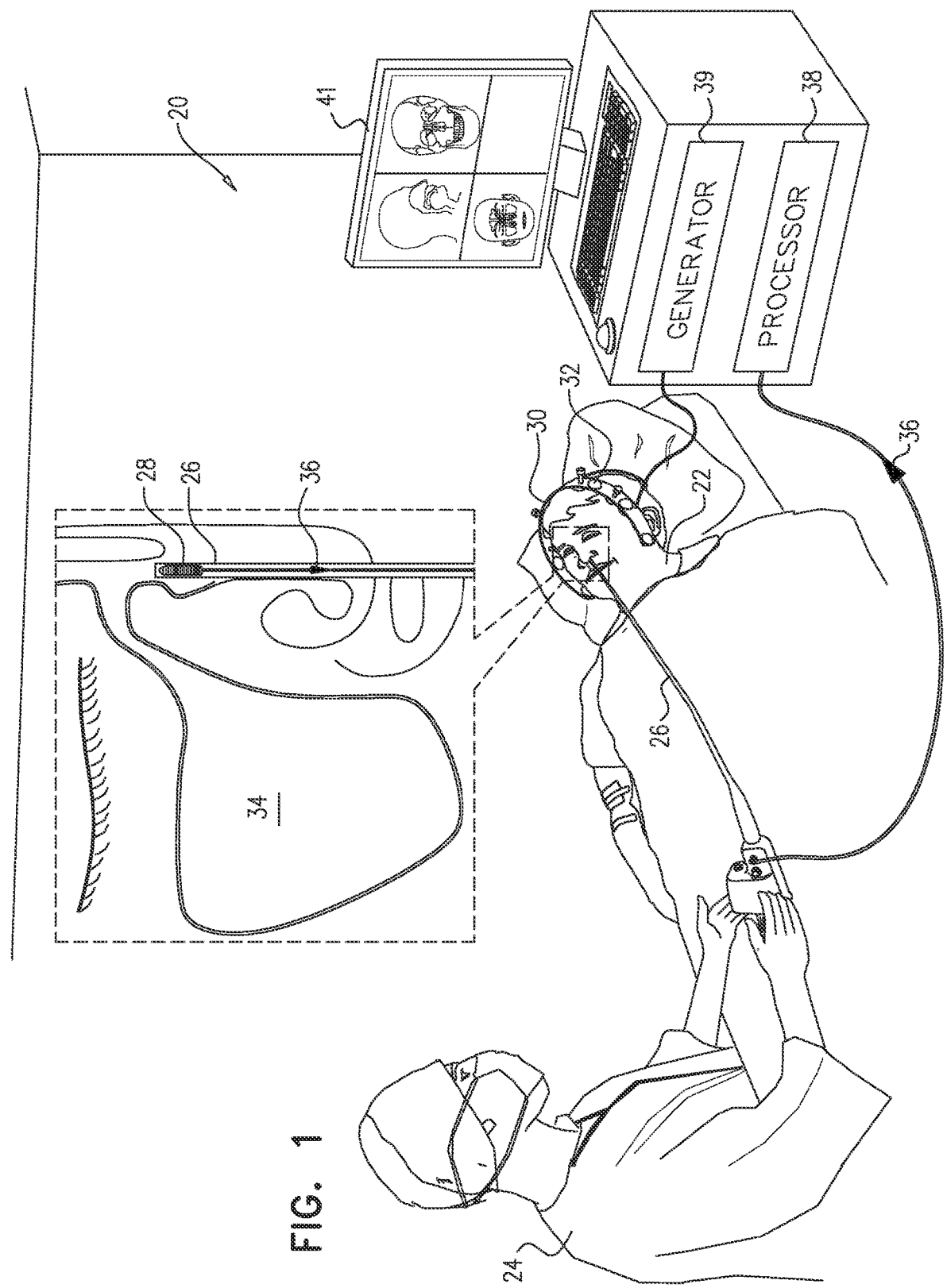
FIG. 1 is a schematic illustration of a method for performing a sinuplasty procedure on a subject, in accordance with some embodiments of the present invention.

When a medical instrument is inserted into a subject for a medical procedure, an operating physician may desire to know the approximate location and/or orientation of the instrument. For example, when performing a sinuplasty procedure, the operating physician may insert a guidewire through a nostril of the subject, and subsequently, use the guidewire to perform the sinuplasty. If the distal portion of the guidewire is at the wrong location within the subject, the sinuplasty procedure may not be successful, and furthermore, may be potentially harmful to the subject; hence, it is often beneficial for the physician to know the approximate location of the distal portion of the guidewire.

One technique that may be employed involves the use of an electromagnetic (EM) tracking sensor, comprising at least one coil and placed at a distal portion of the instrument, to track the instrument. The subject is placed in a magnetic field, such that the sensor generates an electrical signal in response to the magnetic field. The electrical signal is conveyed to a processor. In response to the signal, the processor may track the instrument, i.e., the processor may ascertain the position and/or orientation of the distal portion of the instrument. This technique may be employed for sinuplasty, for example, by placing the tracking sensor within the guidewire lumen, at the distal portion of the guidewire. One challenge, when employing the aforementioned technique, is that the tracking sensor may not be sensitive enough to the magnetic field, especially if the inner diameter of the guidewire imposes constraints on the size of the sensor.

One solution for increasing the sensitivity of a sensor to a magnetic field is to wind the sensor coil around a ferrite core. However, a prior-art ferrite core, consisting of a solid ferrite rod, may be unsuitable for use in applications in which the core is required to have a relatively small diameter. In particular, a solid ferrite rod may easily break if the diameter-to-length ratio of the rod is less than approximately 0.5. (For particularly small rod diameters—e.g., for diameters less than 1 mm—the "critical" diameter-to-length ratio may be even greater than 0.5.) Thus, for a relatively small rod diameter, it may be necessary to limit the length of the rod, to the point that the rod is unable to sufficiently increase the sensitivity of the sensor.

For example, the sinuplasty guidewire mentioned above typically has a relatively small inner diameter, e.g., 0.5-1 mm, such that a ferrite core for placement within the sinuplasty guidewire must likewise have a relatively small diameter. Hence, for sinuplasty applications, a solid ferrite rod may be unsuitable for use, as the rod, in order not to easily break, would need to have a length (e.g., 1-1.5 mm) that renders the rod not sufficiently effective.

Embodiments of the present invention address the aforementioned challenge, by providing a ferrite core that is generally capable of having a relatively small diameter-to-length ratio, without easily breaking. As further described hereinbelow, the ferrite core comprises a tube containing a ferrite powder. Embodiments of the present invention may be used for a sinuplasty procedure, an electrophysiological procedure, or any other suitable type of procedure.

Reference is now made to FIG. 1, which is a schematic illustration of a method 20 for performing a sinuplasty procedure on a subject 22, in accordance with some embodiments of the present invention. (As noted above, embodiments of the present invention may be used for any type of suitable procedure, such that specific references herein to a sinuplasty procedure should be understood as being provided by way of example only.) FIG. 1 shows an operating physician 24 inserting a guidewire 26 into subject 22, through a nostril of the subject. Subsequently to positioning the guidewire within the nasal cavity and/or sinus 34 of the subject, the physician may use guidewire 26 to perform the sinuplasty procedure. For example, the physician may pass a balloon over the guidewire and through the nostril, and subsequently, expand the balloon within the subject, e.g., such as to open the ostium of the subject's sinus.

During the procedure, a clamp 30 is clamped to the subject's head, clamp 30 including a plurality of coils 32. A generator 39, which is connected to clamp 30, drives coils 32 to generate a magnetic field. The field from coils 32 is configured such that the magnetic field at a particular point in space corresponds to a unique location of the point relative to coils 32. In response to the magnetic field, a tracking sensor 28 at the distal portion of guidewire 26 generates an electrical signal 36, which is received by a processor 38. Since signal 36 is indicative of both the position and orientation of sensor 28, processor 38 may track, i.e., ascertain the position and/or orientation of, the guidewire.

Since the position of the clamp is fixed with respect to the subject's head, the magnetic field generated by the coils may be used to track the guidewire, even if the subject moves his head during the procedure. Typically, the position and/or orientation of sensor 28 (and thus of the distal end of guidewire 26) is overlaid and displayed on an image of the subject's head on a display 41.

Typically, as shown in FIG. 1, signal 36 is transferred via a wired connection through the guidewire to the proximal end of the guidewire, and subsequently, to processor 38. In other embodiments, signal 36 is transferred, at least in part, wirelessly.

Reference is now made to FIG. 2, which is a schematic illustration of tracking sensor 28, in accordance with some embodiments of the present invention. Sensor 28 comprises a ferrite core 48, comprising a tube 42 (such as a polyamide tube) having lumen 60 and containing a ferrite powder 44. To manufacture ferrite core 48, ferrite powder 44 is inserted into tube 42, and is compressed within the tube. The compression of powder 44 within the tube helps increase the amount of powder that may be placed within the tube, thus enhancing the ability of the ferrite core to increase the sensitivity of the sensor. Typically, the tube is substantially maximally-filled with the powder (or with powder and bonding material, separate from one another or mixed with one another, as described below), such that the powder generally does not move within the tube, and hence, the ferromagnetic properties of the ferrite core remain generally constant, following manufacture of the ferrite core. Typically, powder 44 comprises iron-carbonyl.

Typically, the ferrite core is generally rigid, i.e., it does not flex in response to the usual forces to which intra-body sensors are subjected during medical procedures. The rigidity of the ferrite core helps the ferromagnetic properties of the ferrite core remain generally constant. Typically, the rigidity of the ferrite core is facilitated by the substantial "maximal filling" of powder within the tube, as described hereinabove. In some embodiments, tube 42 is generally rigid, even prior to being filled with the powder.

Sensor 28 further comprises a coil 46 wound around tube 42. In some embodiments, coil 46 is wound around tube 42 prior to the tube being filled with powder 44. In other embodiments, coil 46 is wound around the tube, or the tube is inserted into the lumen of coil 46, after the tube has been partially or maximally filled with the powder. As shown in FIG. 2, coil 46 may be several layers thick. Coil 46 is typically made of an insulated electrically-conductive wire, e.g., copper wire. Signal 36 is generated by the electrical voltage that is induced across coil 46 by the ambient magnetic field.

Typically, a bonding material 52 is inserted into the tube, along with powder 44. The bonding material helps the ferromagnetic properties of the ferrite core remain generally constant, by inhibiting movement of the powder within the tube. For example, a mixture 50 of ferrite powder 44 and bonding material 52 may be inserted into the tube, mixture 50 typically being compressed within the tube. Alternatively or additionally, the bonding material may be inserted into the tube at at least one end of the tube, thus helping to seal the ferrite powder within the tube.

In some embodiments, no bonding material is inserted into the tube. In such embodiments, following the filling of the tube, the powder is sealed within the tube by sealing the ends of the tube, e.g., using a bonding material.

Typically, the inserting of the ferrite powder and the compressing of the ferrite powder within the tube are performed repeatedly and alternatingly. In other words, a small amount of ferrite powder is inserted into the tube, the powder within the tube is compressed, another small amount of ferrite powder is inserted into the tube, the powder within the tube is again compressed, and so on.

An advantage of ferrite core 48 is that even if the diameter D0 of the core (which is generally the same as the outer diameter of the tube) is small relative to the length L of the core, the ferrite core does not break easily, since the tube provides structural integrity to the core. Thus, D0 may be made relatively small, while maintaining a length L that is generally large enough for the ferrite core to be effective (e.g., L may be greater than 2 mm). For example, with a length L of 3 mm, D0 may be less than 1 mm, e.g., less than 0.8 mm, 0.5 mm, or 0.3 mm, e.g., D0 may be approximately 0.2 mm. (In contrast, a solid ferrite rod having a length of 3 mm may need to have a diameter of more than 1 mm; conversely, for a rod diameter of less than 1 mm, the length of the rod may need to be limited to less than 3 mm, e.g., less than 2 mm.) Alternatively or additionally, the ratio of D0 to L may be less than 0.2, e.g., less than 0.1.

As noted above, the relatively small diameter of the core helps sensor 28 be placed within the lumen of guidewire 26. For example, the total diameter of the sensor, which includes the thickness of the coil, may be less than 1 mm, e.g., less than 0.5 mm. (As noted above, a typical range for the diameter of the guidewire lumen is 0.5-1 mm.)

Although the present description relates mainly to a cylindrical tube, for which the maximal transverse-cross-sectional span S0 of the tube is the diameter D0 of the tube, it is noted that the tube may have any reasonable type of transverse cross-section. Hence, in general, references to "D0" above may be substituted with "S0," when relating to a tube that does not have a circular transverse cross-section.

It is noted that sensor 28 may be used with any suitable medical instrument. For example, sensor 28 may be placed within the lumen of a catheter at a distal portion of the catheter, or coupled to the distal portion of an endoscope or needle. In some embodiments, the central longitudinal axis 54 of the ferrite core is not linear. For example, prior to and/or during the filling of the tube, the tube may be shaped such that central longitudinal axis 54 is not linear. In some applications, a non-linear ferrite core is advantageous, in that the ferrite core may conform to the shape of a non-linearly-shaped medical instrument. For example, some medical procedures use a needle with a curved tip; for such procedures, it may be preferable to couple a curved ferrite core, rather than a linear ferrite core, to the tip of the needle.

Manufacturing a non-linear ferrite core in accordance with embodiments of the present invention is generally easier than manufacturing a non-linear solid rod of ferrite, since the tube may be shaped more easily than a rod.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A tracking sensor at a distal portion of a medical instrument, said tracking sensor configured to determine a location and an orientation of the medical instrument inserted into a subject for a medical procedure, and said tracking sensor providing an electrical signal in response to a magnetic field, said tracking sensor comprising:
a tube having a lumen and a ferrite powder in the lumen, wherein the lumen is substantially maximally-filled with the ferrite powder; and
a coil wound around the tube;
wherein the tube and ferrite powder constitute a ferrite core, the ferrite core having a rigidity such that the ferrite core does not flex in response to usual forces to which the tracking sensor is subjected while inserted into the subject for the medical procedure, and the rigidity of the ferrite core facilitated by the substantial maximal filling of ferrite powder within the tube or a rigidity of the tube.

2. The tracking sensor according to claim 1, wherein the tube has a bonding material inserted therein.

3. The tracking sensor according to claim 2, wherein the lumen is substantially maximally-filled with the ferrite powder and the bonding material.

4. The tracking sensor according to claim 1, wherein the tube has a maximal transverse-cross-sectional span of less than 1 mm.

5. The tracking sensor according to claim 1, wherein the ferrite powder is compressed within the tube.

6. The tracking sensor according to claim 1, wherein the tube is filled with the ferrite powder so that the ferrite powder does not move within the tube.

7. An apparatus, comprising:
a medical instrument; and
at least one tracking sensor for determining a location and an orientation of the medical instrument when the medical instrument is inserted into a subject for a medical procedure, said at least one tracking sensor providing an electrical signal in response to a magnetic field and disposed at a distal portion of the medical instrument, the at least one tracking sensor comprising:
a tube having a lumen and a ferrite powder in the lumen, and
a coil wound around the tube,
wherein the lumen is substantially maximally-filled with the ferrite powder,
wherein the tube and ferrite powder constitute a ferrite core, the ferrite core having a rigidity such that the ferrite core does not flex in response to usual forces to which the tracking sensor is subjected while inserted into the subject for the medical procedure, and the rigidity of the ferrite core facilitated by the substantial maximal filling of ferrite powder within the tube or a rigidity of the tube.

8. The apparatus according to claim 7, wherein the medical instrument comprises a guidewire, and the at least one tracking sensor being disposed within a lumen of the guidewire.

9. The apparatus according to claim 7, wherein the ferrite powder is compressed.

10. The apparatus according to claim 7, wherein the tube is filled with the ferrite powder so that the ferrite powder does not move within the tube.

11. A method for tracking a medical instrument inserted into a subject, comprising:
inserting the medical instrument into the subject, at least one tracking sensor being disposed at a distal portion of the medical instrument, the at least one tracking sensor including a tube having a lumen and a ferrite powder in the lumen, and a coil wound around the tube,
wherein the lumen is substantially maximally-filled with the ferrite powder,
wherein the tube and ferrite powder constitute a ferrite core, the ferrite core having a rigidity such that the ferrite core does not flex in response to usual forces to which the tracking sensor is subjected while inserted into the subject for the medical procedure, and the rigidity of the ferrite core facilitated by the substantial maximal filling of ferrite powder within the tube or a rigidity of the tube;
generating an electrical signal in response to a magnetic field using the at least one tracking sensor; and
tracking the medical instrument in response to the electrical signal using a processor.

12. The method according to claim 11, wherein tracking the medical instrument comprises ascertaining a position of the distal portion of the medical instrument.

13. The method according to claim 11, wherein tracking the medical instrument comprises ascertaining an orientation of the distal portion of the instrument.

14. The method according to claim 11, wherein the medical instrument comprises a guidewire having a lumen therein and wherein the at least one tracking sensor is disposed within the lumen of the guidewire, and the method further comprising inserting the guidewire into the subject.

15. The method according to claim 11, wherein inserting the medical instrument into the subject comprises inserting the medical instrument through a nostril of the subject.

16. The method according to claim 15, further comprising using the medical instrument to perform a sinuplasty procedure on the subject.

17. The method according to claim 11, wherein the ferrite powder is compressed.

18. The method according to claim 11, wherein the tube is filled with the ferrite powder so that the ferrite powder does not move within the tube.

19. The method according to claim 11, further comprising a step of including a clamp, wherein the clamp is configured to be clamped to the subject's head, and the clamp includes coils configured to generate the magnetic field, so that in response to the magnetic field, the at least one tracking sensor generates the electrical signal.

20. A ferrite core, comprising:
a ferrite powder; and
a tube, wherein
the tube and ferrite powder constitute the ferrite core,
the tube is substantially maximally-filled with the ferrite powder,
the ferrite core has a rigidity such that the ferrite core does not flex in response to usual forces to which the ferrite core is subjected while being inserted into a subject for a medical procedure,
the rigidity of the ferrite core is facilitated by the substantial maximal filling of the ferrite powder within the tube or a general rigidity of the tube, and
the tube has a maximal transverse-cross-sectional span of less than 1 mm, containing the ferrite powder.

21. The ferrite core according to claim 20, further comprising a bonding material, wherein the tube further contains the bonding material.

22. The ferrite core according to claim 21, wherein the ferrite powder and the bonding material are mixed with one another within the tube.

23. The ferrite core according to claim 20, wherein maximal transverse-cross-sectional span of the tube is less than 0.5 mm.

24. The ferrite core according to claim 23, wherein the maximal transverse-cross-sectional span of the tube is less than 0.3 mm.

25. The ferrite core according to claim 20, wherein the ferrite powder comprises iron-carbonyl.

26. The ferrite core according to claim 20, wherein a central longitudinal axis of the ferrite core is not linear.

27. The ferrite core according to claim 20, wherein the maximal transverse-cross-sectional span of the tube is a diameter of the tube, the diameter being less than 1 mm.

28. The ferrite core according to claim 20, wherein a ratio of the maximal transverse-cross-sectional span of the tube to a length of the tube is less than 0.2.

29. The ferrite core according to claim 28, wherein the ratio is less than 0.1.

30. The ferrite core according to claim 12, wherein a length of the tube is greater than 2 mm.

* * * * *